United States Patent
Lee et al.

(10) Patent No.: US 9,068,941 B2
(45) Date of Patent: Jun. 30, 2015

(54) APPARATUS FOR MONITORING A DYE SOLUTION TO BE ADSORBED TO A DYE-SENSITIZED SOLAR CELL, AND APPARATUS FOR ADJUSTING THE DYE SOLUTION

(75) Inventors: Chong-chan Lee, Hwasung-si (KR); Yoon-Gil Yim, Hwasung-si (KR)

(73) Assignee: DONGJIN SEMICHEM CO., LTD, Incheon (KR)

( * ) Notice: Subject to any disclaimer, the term of this patent is extended or adjusted under 35 U.S.C. 154(b) by 961 days.

(21) Appl. No.: 13/255,451

(22) PCT Filed: Mar. 8, 2010

(86) PCT No.: PCT/KR2010/001415
§ 371 (c)(1),
(2), (4) Date: Nov. 3, 2011

(87) PCT Pub. No.: WO2010/104294
PCT Pub. Date: Sep. 16, 2010

(65) Prior Publication Data
US 2012/0037270 A1      Feb. 16, 2012

(30) Foreign Application Priority Data
Mar. 10, 2009      (KR) .................. 10-2009-0020112

(51) Int. Cl.
*B65B 3/04*      (2006.01)
*G01N 21/00*      (2006.01)
(Continued)

(52) U.S. Cl.
CPC .... *G01N 21/5907* (2013.01); *G01N 2021/8416* (2013.01); *H01G 9/2031* (2013.01); *H01G 9/2059* (2013.01); *H01G 9/2068* (2013.01);
(Continued)

(58) Field of Classification Search
CPC ... H01G 9/2068; H01G 9/2059; Y02E 10/542
USPC .......................................................... 137/83
See application file for complete search history.

(56) References Cited

U.S. PATENT DOCUMENTS

| 4,427,749 A | * | 1/1984 | Graetzel et al. ............... 429/111 |
| 4,591,550 A | * | 5/1986 | Hafeman et al. ........... 205/777.5 |

(Continued)

FOREIGN PATENT DOCUMENTS

| KR | 10-2008-0054971 | 6/2008 |
| KR | 10-2008-0072425 | 8/2008 |

(Continued)

*Primary Examiner* — John K Fristoe, Jr.
*Assistant Examiner* — Kevin Barss
(74) *Attorney, Agent, or Firm* — Lexyoume IP Meister, PLLC

(57) ABSTRACT

This disclosure relates to a dye solution monitoring device and a dye solution controlling device for a dye-sensitized solar cell, more particularly, to a dye solution monitoring device for a dye-sensitized solar cell comprising a light-absorption device for measuring absorbance of a dye solution for a dye-sensitized solar cell, and a pH measuring device for measuring pH of a dye solution for a dye-sensitized solar cell; and, a dye solution controlling device for a dye-sensitized solar cell further comprising a dye supply device supplying dye of high concentration, and an acid or base supply device for pH control, in addition to the monitoring device.
According to the present invention, a dye adsorption process may be optimized in real time to manufacture a solar cell of high quality with high productivity, maximize utilization of expensive dye, and minimize the waste, thereby reducing production cost.

10 Claims, 2 Drawing Sheets

(51) Int. Cl.
*G01N 31/00* (2006.01)
*G01N 21/59* (2006.01)
*G01N 21/84* (2006.01)
*H01G 9/20* (2006.01)
*H01L 51/00* (2006.01)

(52) U.S. Cl.
CPC .......... *H01L 51/0086* (2013.01); *Y02E 10/542* (2013.01)

(56) References Cited

U.S. PATENT DOCUMENTS

| | | | |
|---|---|---|---|
| 5,500,188 A * | 3/1996 | Hafeman et al. | 204/403.01 |
| 6,559,373 B2 * | 5/2003 | Choi et al. | 136/256 |
| 6,913,713 B2 * | 7/2005 | Chittibabu et al. | 252/501.1 |
| 7,048,436 B2 * | 5/2006 | Mathis | 374/43 |
| 7,972,900 B2 * | 7/2011 | Tiwari et al. | 438/104 |
| 2004/0211458 A1 * | 10/2004 | Gui et al. | 136/244 |
| 2005/0150545 A1 * | 7/2005 | Choi et al. | 136/263 |
| 2006/0249201 A1 * | 11/2006 | Lawandy | 136/263 |
| 2007/0073052 A1 * | 3/2007 | Velusamy et al. | 540/1 |
| 2008/0011351 A1 * | 1/2008 | Diau et al. | 136/256 |
| 2008/0202583 A1 * | 8/2008 | Lee | 136/262 |

FOREIGN PATENT DOCUMENTS

| | | |
|---|---|---|
| KR | 10-2008-0075864 | 8/2008 |
| KR | 10-2008-0079894 | 9/2008 |

\* cited by examiner

APPARATUS FOR MONITORING A DYE SOLUTION TO BE ADSORBED TO A DYE-SENSITIZED SOLAR CELL, AND APPARATUS FOR ADJUSTING THE DYE SOLUTION

BACKGROUND OF THE INVENTION (a) Field of the Invention

The present invention relates to a dye solution monitoring device and a dye solution controlling device for a dye-sensitized solar cell, more particularly, to a dye solution monitoring device and a dye solution controlling device for a dye-sensitized solar cell that may optimize dye adsorption in real time to manufacture a solar cell of high quality with high productivity, maximize utilization of expensive dye, and minimize the waste, thereby reducing production cost, and may manufacture a highly efficient battery, and a method applied to the devices.

(b) Description of the Related Art

Since a dye-sensitized nanoparticle titanium oxide solar cell was developed by Michael Gratzel et al., of EPFL (Ecole Polytechnique F d rale de Lausanne) at 1991, many studies thereon has been progressed. A dye-sensitized solar cell may replace the existing amorphous silicon solar cell because it has high efficiency and remarkably low manufacture cost compared to the existing silicon type solar cell, and unlike the silicon solar cell, it is a photoelectrochemical solar cell consisting of a dye molecule capable of absorbing visible light to generate electron-hole pairs and transition metal oxide transferring the produced electrons.

In general, a unit cell of a dye-sensitized solar cell includes upper and lower transparent substrates (generally, glass), a conductive transparent electrode made of transparent conductive oxide (TCO) respectively formed on the transparent substrates, a dye-adsorbed transition metal oxide porous layer on one conductive transparent electrode corresponding to a first electrode (working electrode), a catalyst thin film electrode (predominantly, Pt) on the other conductive transparent electrode corresponding to a second electrode (catalyst electrode), and electrolyte filled between the transition metal oxide (for example, $TiO_2$) and the catalyst thin film electrode. Thus, the dye-sensitized solar cell basically consists of a working electrode substrate on which photoelectrode ($TiO_2$) material including dyes receiving light to generate electrons attached thereto are coated, a catalyst electrode substrate supplying electrons, and electrolyte supplying electrons to oxidized dyes therebetween.

The efficiency and the production cost of the solar cell are largely influenced by the adsorption amount of the adsorption dyes having excellent properties on the transition metal oxide porous layer. Specifically, as the adsorption amount is high and the properties of the absorbed dyes are excellent, photoelectric efficiency of the solar cell increases, expensive dyes are efficiently used, and thus, waste ratio of non-adsorbed dyes is lowered to reduce production cost.

However, in the prior art, to increase adsorption rate, newly synthesized dye is adjusted to a concentration with best adsorption rate, to prepare a dye solution, and a cell of a solar cell is impregnated therewith. Thus, as an adsorption process progresses for a plurality of cells, the concentration changes to decrease adsorption rate, and the remaining dye solution should be discarded, and thus, waste ratio is high to cause serious waste of dyes. Therefore, to improve this, the concentration of a dye solution is controlled; however, light absorption coefficient is gradually lowered due to modification of dyes during the adsorption process compared to using of initial solution, and thus, manufacturing of an excellent solar cell may not be optimized only by concentration control, and in the case of manual concentration control, a dye adsorption process may not be continuously progressed to decrease productivity.

Accordingly, there is a need for development of dye solution monitoring device and method that may overcome the problems.

SUMMARY OF THE INVENTION

Figure 1:
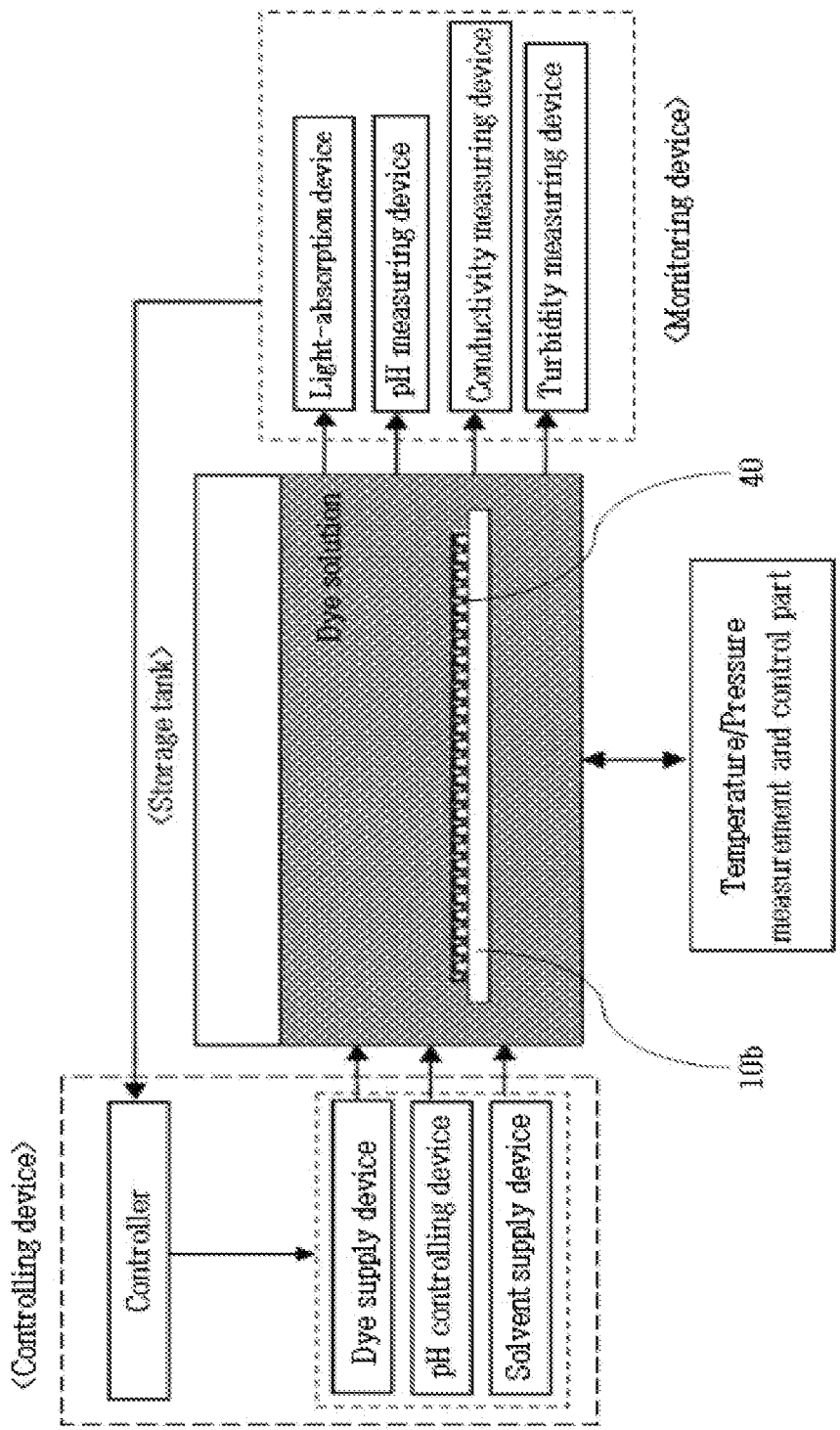
FIG. 1 is a system schematic view of a dye adsorption device for a dye-sensitized solar cell according to one example of the invention (TCO layer and catalyst layer, and the like are not shown for simplification).

In order to solve the problems of the prior art, the present invention provides a dye solution monitoring device and a dye solution controlling device for a dye-sensitized solar cell that may optimize dye adsorption in real time to manufacture a solar cell of high quality with high productivity, maximize utilization of expensive dye, and minimize the waste, thereby reducing production cost, and a dye management method applied to the devices.

The present invention provides a dye solution monitoring device for a dye-sensitized solar cell comprising a light-absorption device for measuring absorbance of a dye solution for a dye-sensitized solar cell; and a pH measuring device for measuring pH of a dye solution for a dye-sensitized solar cell.

The present invention also provides a dye solution control device for a dye-sensitized solar cell comprising a storage tank of the dye solution;

the above described dye solution monitoring device for a dye-sensitized solar cell;

a dye supply device for supplying the storage tank with a dye solution of higher concentration than the dye solution in the storage bath a pH control device for supplying the storage tank with acid or base; and a controller controlling the dye supply device and the pH control device according to the absorbance and pH value obtained from the monitoring device.

The present invention also provides a dye adsorption device for a dye-sensitized solar cell comprising a storage tank of the dye solution, having a transfer apparatus for entrance and exit of a dye support;

the above described dye solution monitoring device for a dye-sensitized solar cell;

a dye supply device supplying the storage tank with a dye solution of higher concentration than the dye solution in the storage tank;

a pH control device supplying the storage tank with acid or base;

a temperature control part measuring and controlling temperature of the dye solution in the storage tank;

a pressure control part measuring and controlling pressure of the dye solution in the storage tank; and a controller controlling the dye supply device and the pH control device according to absorbance and pH values obtained from the monitoring device.

The present invention also provides a dye adsorption device for a dye-sensitized solar cell comprising a storage tank of the dye solution, having a transfer line circulating the dye solution to a module of the dye-sensitized solar cell;

the above described dye solution monitoring device for a dye-sensitized solar cell;

a dye supply device supplying the storage tank with a dye solution of higher concentration than the dyes solution in the storage tank;

a pH control device supplying the storage tank with acid or base;

a temperature control part measuring and controlling temperature of the dye solution in the transfer line or temperature of the dye-sensitized solar cell module;

a pressure control part measuring and controlling pressure of the dye solution in the transfer line or pressure in the dye-sensitized solar cell module; and a controller controlling the dye supply device and the pH control device according to absorbance and pH values obtained from the monitoring device.

The present invention also provides a method for monitoring a dye solution for a dye-sensitized solar cell, wherein measurement of absorbance of the dye solution for a dye-sensitized solar cell is conducted simultaneously with measurement of pH of the dye solution for a dye-sensitized solar cell, and a method for controlling a dyes solution for a dye-sensitized solar cell applying the above monitoring method.

According to a dye solution monitoring device and a dye solution controlling device for a dye-sensitized solar cell and a dye management method applied to the devices, a dye adsorption process may be optimized in real time to manufacture a solar cell of high quality with high productivity, maximize utilization of expensive dye, and minimize the waste, thereby reducing production cost, and decreasing environmental pollution.

DETAILED DESCRIPTION OF THE EMBODIMENTS

Hereinafter, the present invention will be explained in detail

The dye solution monitoring device for a dye-sensitized solar cell includes a light-absorption device for measuring absorbance of a dye solution for a dye-sensitized solar cell, and a pH measuring device for measuring pH of a dye solution for a dye-sensitized solar cell.

It will be explained in detail with reference to drawings.

Specifically, the present invention monitors the state of the dye solution in order to effectively adsorb dyes in a porous layer of transition metal oxide such as $TiO_2$ for manufacturing of a dye-sensitized solar cell, and for this, is equipped with a light-absorption device measuring absorbance of a dye solution for a dye-sensitized solar cell for monitoring dye concentration in the dye solution, in addition to a dye solution monitoring device for a dye-sensitized solar cell of the prior art. Namely, from understanding that the dye solution for a dye-sensitized solar cell of the present invention has a light absorption function, the light absorption device is allowed to measure the concentration of dye having a light absorption function by irradiating light generated through a light source to dye, measuring remaining light except those absorbed in the dye, thereby measuring absorbance of the dye solution.

Preferably, the light source of the light absorption device may be in the wavelength band of light which is absorbed by dye because it is easy to measure the concentration. It may be in the wavelength band having maximum absorption rate of dye to be measured, and in some cases, it may be adjusted to other wavelength band where absorbance change is sensitive according to concentration. Specifically, a light source applied to the light-absorption device may have wavelength of 175 nm to 3300 nm, or may be a UV light source, and thereby, concentration change may be sensitively detected.

And, as the adsorption process of dye for a dye-sensitized solar cell progresses, the state of the dye solution changes, which causes modification of dye, or render it impossible to further adsorb dyes even if dye concentration is high. Thus, optimum adsorption condition may not be maintained only by concentration monitoring, and the state of the dye solution should be managed together. Since the state of the dye solution is generally influenced by acidity or basicity of the dye solution, the monitoring device of the present invention includes a pH measuring device measuring pH of the dye solution for a dye-sensitized solar cell in order to manage the state of the dye solution. The pH measuring device may include various forms, and it may be preferably applied to dyes wherein acidity or basicity of the dye solution changes during the adsorption process (specific examples thereof may include organic dye, organometallic dye, and the like, and if pH changes as the adsorption progresses, adsorption rate of dyes or adsorbed dyes may be changed, and thus, pH monitoring is required during the progress of adsorption. Particularly, pH change may influence on the adsorption rate of the organic dye because reaction of dye, for example, reactivity of —COOH may differ according to pH of the dye solution, and it may also influence on the adsorption rate of the organimetallic dye or change the structure of the dye to decrease battery efficiency.), more preferably, ruthenium-based dyes wherein pH of the dye solution changes to change the structure of dye as the adsorption process continuously progresses, still more preferably, ruthenium (Ru)-based dyes having TBA that is deteriorated according to acidity of the dye solution, such as separation of TBA of initial dye, further attachment of TBA to modify initial dye to dye having lower efficiency.

Figure 2:
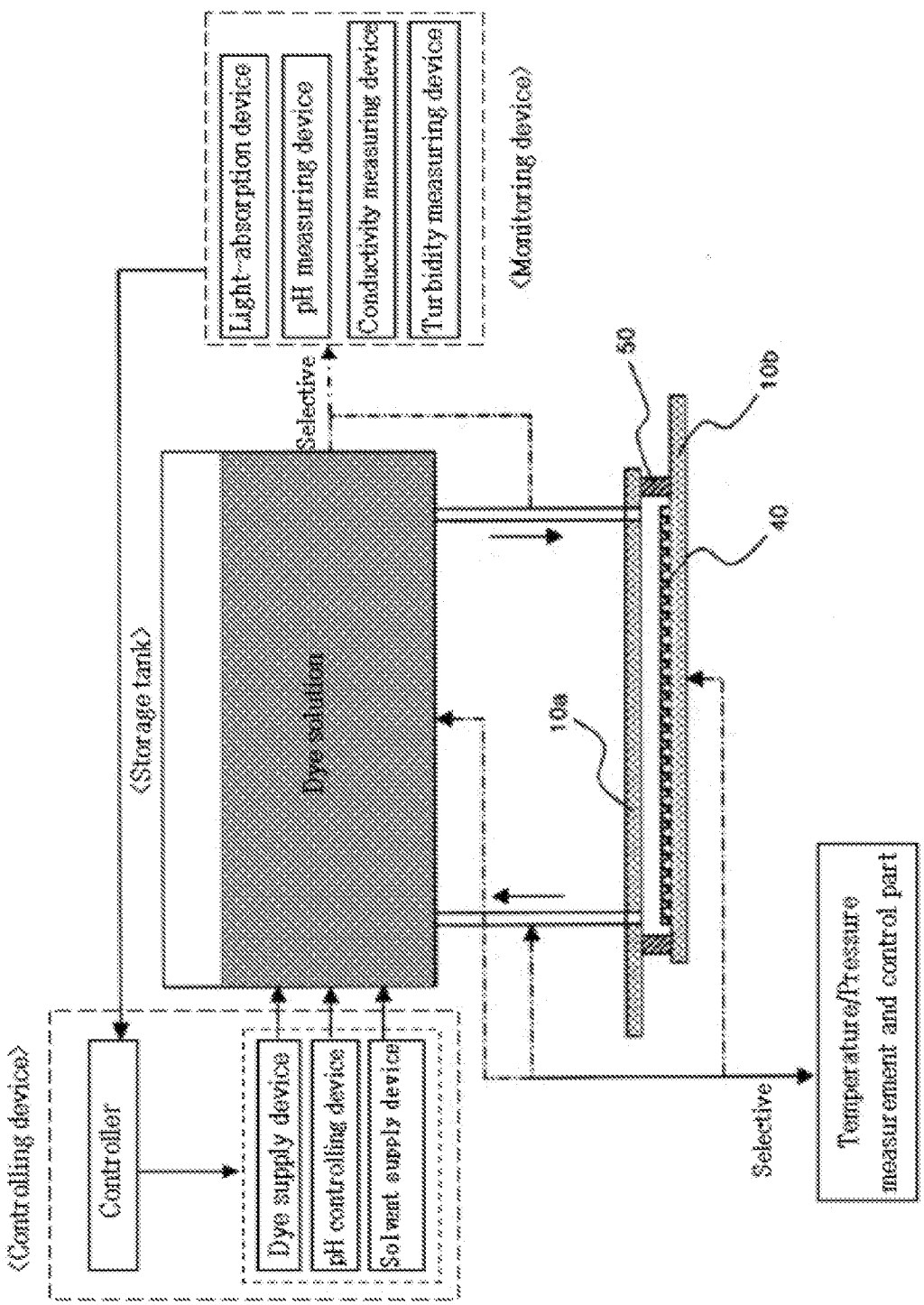
FIG. 2 is a system schematic view of a dye adsorption device for a dye-sensitized solar cell according to another example of the invention. (TCO layer and catalyst layer, and the like are not shown for simplification).

To measure absorbance and pH, the light absorption device and the pH measuring device may be installed as shown in FIG. 1 and FIG. 2, or a sample of the dye solution may be collected to measure absorbance and pH. Specifically, the light absorption device may directly measure absorbance from a storage tank or transfer line (inlet or outlet line) of the dye solution, or it may collect a sample from the storage tank or transfer line to measure absorbance, and the pH measuring device may directly measure pH from the storage tank or transfer line (inlet or outlet line) of the dye solution, or it may collect a sample from the storage tank or transfer line to measure pH, and thereby the state of the dye solution may be monitored in real time, and a continuous process may be conducted.

In addition, the monitoring device may further include an additional measuring device measuring turbidity or conductivity of the dye solution for a dye-sensitized solar cell, as shown. Thereby, abnormality of the dye solution may be identified, and the degree of pollution by foreign substance in the dye solution may be figured out by measuring turbidity to prevent adsorption of foreign substance beforehand.

The present invention also provides a dye solution control device for a dye-sensitized solar cell comprising a storage tank of the dye solution; the above described dye solution monitoring device for a dye-sensitized solar cell; a dye supply device for supplying the storage tank with a dye solution of higher concentration than the dye solution in the storage bath; a pH control device for supplying the storage tank with acid or base; and, a controller controlling the dye supply device and the pH control device according to the absorbance and pH value obtained from the monitoring device.

A specific example thereof is as shown in FIG. 1 and FIG. 2. Specifically, according to the state of the dye solution monitored by the monitoring device, it should be changed to a state where optimum adsorption may be achieved. Therefore, if the dye concentration is lower than optimum adsorption condition, a dye supply device is operated to supply a dye solution of higher concentration than the dye solution in the storage tank; if the acidity of the solution is increased by dye adsorption, the pH control device is operated so as to supply base to control pH; and if the basicity is increased, the pH control device is operated so as to supply acid to control pH. Since the control of concentration and pH is feedback controlled by the controller, the dye solution in the storage tank is always controlled with optimum adsorption condition in real time.

For example, for a dye solution containing ruthenium-based dyes, if UV is irradiated and UV absorption rate is below a certain degree, it means that dye concentration is decreased, and in this case, to increase dye concentration such that sufficient absorption may be achieved, a dye solution of high concentration is added to adjust to appropriate concentration.

And, for ruthenium-based dyes, pH gradually changes as a dye adsorption process progresses, which influences on the property of a manufactured solar cell in two ways. First, N719, a representative example of ruthenium-based dye, has an original structure wherein two TBA cations are selectively adhered. And, if pH of the dye solution changes by the increase of adsorption number or other causes, the TBA cat ions adhered to N719 may be dissociated to change into N3 dye form wherein TBA is not adhered (if pH decreases), or additional TBA cations may be adhered to N719 to change into another dye form (if pH increases). This means that the originally supplied N719 is modified into another dye form having decreased efficiency and adsorbed, thus causing deterioration of a dye-sensitized solar cell performance. And, increase in the concentration of the dissociated TBA cations may influence on $TiO_2$ to influence on current or voltage value, thus causing deterioration of a dye-sensitized solar cell performance. Therefore, to prevent dissociation of TBA cat ions, which modifies the original molecular structure of N719, acid or base is added to modify pH of the dye solution to appropriate level.

Namely, since the present invention simultaneously conducts concentration and pH control in real time, optimum adsorption conditions are constantly maintained during a continuous adsorption process to increase adsorption rate of dyes having excellent properties and increase applicability of dyes having excellent properties.

Further, the concentration of the dye solution in the storage tank may excessively be increased due to malfunction of the dye supply device, and the like, and the amount of the dye solution may become insufficient. Thus, to prepare for this, the dye control device may further include a solvent supply device supplying the storage tank with a solvent of the dye solution, and the controller may be allowed to control the dye supply device, the pH control device and the solvent supply device according to the absorbance and pH values obtained from the monitoring device. Specifically, if the concentration of the dye solution is high, a solvent is additionally supplied to control the concentration of the dye solution to optimum concentration, and if the dye solution is insufficient, a dye solution of high concentration is supplied from the dye supply device, and a solvent is supplied to provide a new solution of optimum concentration.

The present invention also provides a dye adsorption device for a dye-sensitized solar cell, which includes the case of FIG. 1 wherein adsorption is progressed before assembly of a solar cell, and the case of FIG. 2 wherein adsorption is progressed after assembly of a unit cell.

Specifically, if adsorption is progressed for a unit cell of a dye-sensitized solar cell including a transition metal oxide layer 40 and a lower transparent substrate 10b in the manner as shown in FIG. 1, the device may include a storage tank of the dye solution, having a transfer apparatus for entrance and exit of a dye support; a dye solution monitoring device for a dye-sensitized solar cell; a dye supply device supplying the storage tank with a dye solution of higher concentration than the dye solution in the storage tank; a pH control device supplying the storage tank with acid or base; a temperature control part measuring and controlling temperature of the dye solution in the storage tank; a pressure control part measuring and controlling pressure of the dye solution in the storage tank; and a controller controlling the dye supply device and the pH control device according to absorbance and pH values obtained from the monitoring device.

And, if adsorption is progressed for a unit cell of a dye-sensitized solar cell including an upper transparent substrate 10a, a lower transparent substrate 10b, and encapsulating portions 50 between the upper and lower transparent substrates thereby encapsulating a transition metal oxide layer 40 in the manner as shown in FIG. 2, the device may include a storage tank of the dye solution, having a transfer line circulating the dye solution to a module of the dye-sensitized solar cell; a dye solution monitoring device for a dye-sensitized solar cell; a dye supply device supplying the storage tank with a dye solution of higher concentration than the dyes solution in the storage tank; a pH control device supplying the storage tank with acid or base; a temperature control part measuring and controlling temperature of the dye solution in the transfer line or temperature of the dye-sensitized solar cell module; a pressure control part measuring and controlling pressure of the dye solution in the transfer line or pressure in the dye-sensitized solar cell module; and a controller controlling the dye supply device and the pH control device according to absorbance and pH values obtained from the monitoring device.

Namely, to optimize adsorption condition, it is required to optimize adsorption process conditions as well as dye solution conditions, and for this, a temperature control part and a pressure control part for controlling temperature and pressure of the adsorption process are additionally included. In the temperature control part, temperature condition of approximately 50° C. is established and temperature is controlled for common ruthenium-based dyes, and in the pressure control part, high pressure condition may be advantageously applied because it is favorable for adsorption. Additionally, for uniform mixing of the added materials, an agitation device may be further included inside the storage tank, and the like.

As shown in the drawings, the monitoring device may obtain a dye solution from various parts for monitoring of the state of dye, which may be selectively or simultaneously conducted, and may be conducted directly from the indicated part or by sampling.

Specifically, the temperature control part (temperature measuring and controlling part) of FIG. 1 is equipped with a separate temperature measuring device and heating or cooling device in the storage tank, and may control the temperature of the dye solution in the storage tank with a temperature favorable for adsorption as a target value. And, the temperature control part of FIG. 2 may control the temperature as explained above if temperature of a dye solution in the storage tank is to be controlled; if temperature of a dye solution of the transfer line is to be controlled, it may be equipped with a temperature measuring device and a heating or cooling device in the transfer line, or equipped with a heating or cooling device in the storage tank, and control the temperature; and if temperature is to be controlled in a cell where adsorption is substantially achieved, a temperature measuring device may be attached in the storage tank, the transfer line or the cell, and a heating or cooling device may be attached in the storage tank, the transfer line or the cell.

The pressure control part (pressure measuring and controlling part) of FIG. 1 is equipped with separate pressure measuring device and decompression or pressure device (pump and valve, and the like), measures pressure thereby, and controls pressure of the dye solution in the storage tank with a pressure favorable for adsorption as a target value, and in this case, the storage tank should be a pressure vessel. And, the pressure control part of FIG. 2 may control as explained above if pressure of the dye solution in the storage tank is to be controlled; if pressure of the dye solution of the transfer line is to be controlled, it is equipped with a pressure measuring device or decompression/pressure device for the transfer line, or equipped with a decompression/pressure device in the storage tank, and controls the pressure; and, if pressure of a cell where adsorption is substantially achieved is to be controlled, a pressure measuring device may be attached to the storage tank, transfer line or cell, and a pump and a valve may be attached such that a decompression/pressure device may be controlled with reference to the storage tank, transfer line or cell. In this case, the device may be allowed to further control a solvent, and for this, the dye adsorption device may further include a solvent supply device supplying the storage tank with a solvent of the dye solution, and the controller may control the dye supply part, pH control device and solvent supply part according to absorbance and pH values obtained from the monitoring device. In addition, for uniform mixing of added material, an agitation device may be further included inside the storage tank, and the like.

In addition, the present invention provides a monitoring method and controlling method applied to the monitoring device, control device and adsorption device, specifically to a method for monitoring a dye solution for a dye-sensitized solar cell, wherein measurement of absorbance of the dye solution for a dye-sensitized solar cell is conducted simultaneously with measurement of pH of the dye solution for a dye-sensitized solar cell, thereby obtaining higher adsorption effect than the existing monitoring of concentration.

The dyes of the dye solution may be preferably those wherein acidity or basicity is changed during the adsorption process of the dye solution (for example, various organic dyes and organometallic dyes), more specifically, the dye may include ruthenium-based dyes, for example, ruthenium-based dyes having TBA such as N719, and the like.

And, the method for controlling dye for a dye-sensitized solar cell may include monitoring the dye solution for a dye-sensitized solar cell from a storage tank by the above described method for monitoring (a dye solution for a dye-sensitized solar cell), and supplying the storage tank with a dye solution of higher concentration than the dye solution in the storage tank, or with acid or base, according to absorbance and pH values obtained by the monitoring.

Detailed explanations thereof are skipped because they are explained in detail in the description of the devices. In the method for controlling a dye solution for a dye-sensitized solar cell, a control element supplying a solvent may be further added as explained above, which may include monitoring a dye solution for a dye-sensitized solar cell from a storage tank by the above described method for monitoring (a dye solution for a dye-sensitized solar cell), and supplying the storage tank with a dye solution of higher concentration than the dye solution in the storage tank, with acid or base, or with a solvent of the dye solution, according to absorbance and pH values obtained by the monitoring.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A dye solution control device for a dye-sensitized solar cell comprising:
    a storage tank of the dye solution;
    a dye solution monitoring device for a dye-sensitized solar cell comprising a light-absorption device for measuring absorbance from the storage tank or a transfer line of a dye solution, or collecting a sample from the storage tank or the transfer line and measuring absorbance therefrom wherein the dye solution comprises a ruthenium (Ru)-based dye having TBA (Terabutyl Ammonium) of which the acidity or basicity changes during the absorption process and wherein molar concentration of dye is measured through a change in UV absorbance rate by irradiating light to the dye using a UV light source equipped in the light-absorption device and a pH measuring device for measuring pH from the storage tank or the transfer line of the dye solution, or collecting a sample collected from the storage tank or the transfer line and measuring pH therefrom;
    a dye supply device for supplying the storage tank with a dye solution of higher concentration than the dye solution in the storage bath;
    a pH control device for controlling the pH by supplying base to the storage tank in case that the acidity of the dye solution is increased and supplying acid in case that the basicity is increased and wherein the pH control device controls the pH of the dye solution by adding acid or base to the storage tank in order to prevent TBA cations adhered to the dye from being dissociated; and
    a controller controlling the dye supply device and the pH control device according to the absorbance and pH values obtained from the monitoring device.

2. The dye solution control device for a dye-sensitized solar cell according to claim 1, wherein the device further comprises a solvent supply device supplying the storage tank with a solvent of the dye solution, and
    the controller controls the dye supply device, the pH control device and the solvent supply device according to the absorbance and pH values obtained from the monitoring device.

3. The dye solution control device for a dye-sensitized solar cell according to claim 1, wherein the light source applied to the light-absorption device has a wavelength of 175 nm to 3300 nm, or is an UV light source.

4. The dye solution control device for a dye-sensitized solar cell according to claim 1, wherein the dye solution monitoring device further comprises an additional measuring device for measuring turbidity or conductivity of the dye solution.

5. A dye adsorption device for a dye-sensitized solar cell comprising
    a storage tank of the dye solution, having a transfer apparatus for entrance and exit of a dye support;

the dye solution monitoring device for a dye-sensitized solar comprising a light-absorption device for measuring absorbance from the storage tank or a transfer line of a dye solution, or collecting a sample from the storage tank or the transfer line and measuring absorbance therefrom wherein the dye solution comprises a ruthenium (Ru)-based dye having TBA (Terabutyl Ammonium) of which the acidity or basicity changes during the absorption process and molar concentration of dye is measured through a change in UV absorbance rate by irradiating light to the dye using a UV light source equipped in the light-absorption device and a pH measuring device for measuring pH from a storage tank or a transfer line of the dye solution, or collecting a sample collected from the storage tank or the transfer line and measuring pH therefrom;

a dye supply device supplying the storage tank with a dye solution of higher concentration than the dye solution in the storage tank;

a pH control device controlling the pH by supplying base to the storage tank in case that the acidity of the dye solution is increased and supplying acid in case that the basicity is increased and wherein the pH control device controls the pH of the dye solution by adding acid or base to the storage tank in order to prevent TBA cations adhered to the dye from being dissociated;

a temperature control part measuring and controlling temperature of the dye solution in the storage tank;

a pressure control part measuring and controlling pressure of the dye solution in the storage tank; and a controller controlling the dye supply device and the pH control device according to absorbance and pH values obtained from the monitoring device.

6. The dye adsorption device for a dye-sensitized solar cell according to claim 5, wherein the device further comprises a solvent supply device supplying the storage tank with a solvent of the dye solution, and the controller controls the dye supply device, the pH control device and the solvent supply device according to absorbance and pH values obtained from the monitoring device.

7. A dye adsorption device for a dye-sensitized solar cell comprising a storage tank of the dye solution, having a transfer line circulating the dye solution to a module of the dye-sensitized solar cell;

the dye solution monitoring device for a dye-sensitized solar comprising a light-absorption device for measuring absorbance from the storage tank or the transfer line of a dye solution, or collecting a sample from the storage tank or the transfer line and measuring absorbance therefrom wherein the dye solution comprises a ruthenium (Ru)-based dye having TBA (Terabutyl Ammonium) of which the acidity or basicity changes during the absorption process and wherein molar concentration of dye is measured through a change in UV absorbance rate by irradiating light to the dye using a UV light source equipped in the light-absorption device and a pH measuring device for measuring pH from the storage tank or the transfer line of the dye solution, or collecting a sample collected from the storage tank or the transfer line and measuring pH therefrom;

a dye supply device supplying the storage tank with a dye solution of higher concentration than the dyes solution in the storage tank;

a pH control device controlling the pH by supplying base to the storage tank in case that the acidity of the dye solution is increased and supplying acid in case that the basicity is increased and wherein the pH control device controls the pH of the dye solution by adding acid or base to the storage tank in order to prevent TBA cations adhered to the dye from being dissociated;

a temperature control part measuring and controlling temperature of the dye solution in the transfer line or temperature of the dye-sensitized solar cell module;

a pressure control part measuring and controlling pressure of the dye solution in the transfer line or pressure in the dye-sensitized solar cell module; and a controller controlling the dye supply device and the pH control device according to absorbance and pH values obtained from the monitoring device.

8. The dye adsorption device for a dye-sensitized solar cell according to claim 7, wherein the device further comprises a solvent supply device supplying the storage tank with a solvent of the dye solution, and the controller controls the dye supply device, the pH control device, and the solvent supply device according to absorbance and pH values obtained from the monitoring device.

9. A method for controlling a dye solution for a dye-sensitized solar cell, wherein the dye solution for a dye-sensitized solar cell from a storage tank is monitored by simultaneously measuring absorbance of the dye solution for a dye-sensitized solar cell measuring the pH of the dye solution for a dye-sensitized solar cell, wherein molar concentration of dye is measured through a change in UV absorbance rate by irradiating light to the dye using a UV light source and wherein the dye solution comprises a ruthenium (Ru)-based dye having TBA (Terabutyl Ammonium) of which the acidity or basicity changes during the absorption process, and the storage tank is supplied with a dye solution of higher concentration than the dye solution in the storage tank, or with acid or base, according to absorbance and pH values obtained by the monitoring, wherein base is supplied to the storage tank in case that the acidity of the dye solution is increased and acid is supplied to the storage tank in case that the basicity is increased and wherein acid or base is supplied to the storage tank in order to prevent TBA cations adhered to the dye from being dissociated.

10. A method for controlling a dye solution for a dye-sensitized solar cell, wherein the dye solution for a dye-sensitized solar cell from a storage tank is monitored by the method according to claim 9, and the storage tank is supplied with a dye solution of higher concentration than the dye solution in the storage tank, with acid or base, or with a solvent of the dye solution, according to absorbance and pH values obtained by the monitoring.

* * * * *